United States Patent
Ionasec et al.

(10) Patent No.: US 9,033,887 B2
(45) Date of Patent: May 19, 2015

(54) MITRAL VALVE DETECTION FOR TRANSTHORACIC ECHOCARDIOGRAPHY

(71) Applicants: Razvan Ioan Ionasec, Princeton, NJ (US); Dime Vitanovski, Augsburg (DE); Yang Wang, Princeton, NJ (US); Bogdan Georgescu, Plainsboro, NJ (US); Ingmar Voigt, Erlangen (DE); Saurabh Datta, Pleasanton, CA (US); Dorin Comaniciu, Princeton Junction, NJ (US)

(72) Inventors: Razvan Ioan Ionasec, Princeton, NJ (US); Dime Vitanovski, Augsburg (DE); Yang Wang, Princeton, NJ (US); Bogdan Georgescu, Plainsboro, NJ (US); Ingmar Voigt, Erlangen (DE); Saurabh Datta, Pleasanton, CA (US); Dorin Comaniciu, Princeton Junction, NJ (US)

(73) Assignees: Siemens Corporation, Iselin, NJ (US); Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 167 days.

(21) Appl. No.: 13/905,690

(22) Filed: May 30, 2013

(65) Prior Publication Data

US 2014/0052001 A1 Feb. 20, 2014

Related U.S. Application Data

(60) Provisional application No. 61/653,542, filed on May 31, 2012.

(51) Int. Cl.
*A61B 8/06* (2006.01)
*A61B 5/00* (2006.01)
*A61B 8/08* (2006.01)
(Continued)

(52) U.S. Cl.
CPC .............. *A61B 8/065* (2013.01); *A61B 8/463* (2013.01); *A61B 8/14* (2013.01); *A61B 8/488* (2013.01); *A61B 8/5223* (2013.01); *A61B 5/7264* (2013.01); *A61B 8/466* (2013.01); *A61B 5/1075* (2013.01); *A61B 8/085* (2013.01); *A61B 8/486* (2013.01)

(58) Field of Classification Search
CPC .... A61B 5/1075; A61B 5/7264; A61B 8/085; A61B 8/14; A61B 8/463; A61B 8/466; A61B 8/486; A61B 8/488; A61B 8/5223
See application file for complete search history.

(56) References Cited

U.S. PATENT DOCUMENTS

| 7,702,596 B2 | 4/2010 | Tu et al. |
| 7,916,919 B2 | 3/2011 | Zheng et al. |
| 8,920,322 B2 * | 12/2014 | Mansi et al. .................. 600/437 |

OTHER PUBLICATIONS

F. Maisano et al., "The edge-to-edge technique: a simplified method to correct mitral insufficiency," Euro J. Cardio-thoracic Surgery, 13(3), pp. 240-245, 1998.

(Continued)

*Primary Examiner* — Michael Rozanski

(57) ABSTRACT

A mitral valve is detected in transthoracic echocardiography. The ultrasound transducer is positioned against the chest of the patient rather than being inserted within the patient. While data acquired from such scanning may be noisier or have less resolution, the mitral valve may still be automatically detected. Using both B-mode data representing tissue as well as flow data representing the regurgitant jet, the mitral valve may be detected automatically with a machine-learnt classifier. A series of classifiers may be used, such as determining a position and orientation of a valve region with one classifier, determining a regurgitant orifice with another classifier, and locating mitral valve anatomy with a third classifier. One or more features for some of the classifiers may be calculated based on the orientation of the valve region.

12 Claims, 3 Drawing Sheets

(51) Int. Cl.
*A61B 8/00* (2006.01)
*A61B 8/14* (2006.01)
*A61B 5/107* (2006.01)

(56) References Cited

OTHER PUBLICATIONS

T. Feldman et al., "Percutaneous mitral repair with the mitraclip system safety and midterm durability in the initial EVEREST (Endovascular Valve Edge-to-Edge Study) cohort," J. Am. Coll. Cardiol, 54(6), pp. 686-694, 2009.

T. Mansi et al., "Towards patient-specific finite-element simulation of mitraclip procedure," In: MICCAI, vol. 1, pp. 452-459, 2011.

R. Lang et al., "Eae/ase recommendations for image acquisition and display using three-dimensional echocardiography," European Heart Journal of Cardiovascular Imaging, 13(1), pp. 1-46, 2012.

F. Veronesi et al., "Semi-automatic tracking for mitral annulus dynamic analysis using real-time 3d echocardiography," In: Computers in Cardiology, pp. 113-116, 2006.

R. J. Schneider et al., "Patient-specific mitral leaflet segmentation from 4d ultrasound," In: MICCAI, vol. 3, pp. 520-527, 2011.

R. I. Ionasec et al., "Patient-specific modeling and quantification of the aortic and mitral valves from 4d cardiac ct and tee," In: IEEE Transaction on Medical Imaging, in press, 2010.

L. Grady et al., "Regurgitation quantification using 3d pisa in volume echocardiography," In: MICCAI, vol. 3, pp. 512-519, 2011.

Z. Tu, "Probabilistic boosting-tree: Learning discriminative methods for classification, recognition, and clustering," In: ICCV, 2005.

Y. Zheng et al., "Four-chamber heart modeling and automatic segmentation for 3-d cardiac ct volumes using marginal space learning and steerable features," IEEE Transactions on Medical Imaging, 27(11), pp. 1668-1681, 2008.

Z. Tu et al., "Probabilistic 3d polyp detection in ct images: The role of sample alignment," In: CVPR, vol. 2, pp. 1544-1551, 2006.

F. L. Bookstein, "Principal warps: Thin-plate splines and the decomposition of deformations," PAMI, 11(6), pp. 567-585, 1989.

\* cited by examiner

MITRAL VALVE DETECTION FOR TRANSTHORACIC ECHOCARDIOGRAPHY

RELATED APPLICATIONS

The present patent document claims the benefit of the filing dates under 35 U.S.C. §119(e) of Provisional U.S. Patent Application Ser. No. 61/653,542, filed May 31, 2012, which is hereby incorporated by reference.

BACKGROUND

The present embodiments relate to mitral valve detection. The mitral valve (MV), located between the left atrium (LA) and the left ventricle (LV), controls the unidirectional blood flow from the LA towards the LV. The MV is a complex cardiac structure including two leaflets, the mitral annulus and tendineae chordae. The leaflets are attached to the left heart through the fibrous mitral annulus, whereas the other extremity, called the free-edge, is tethered to the papillary muscles through the tendineae chordae. During diastole, the leaflets open as the blood enters the LV. When the myocardium starts to contract, the leaflets close to prevent the blood from going back to the atrium.

Mitral valve disease is one of the most common heart valve diseases, with a prevalence increasing with age. MV regurgitation or mitral insufficiency is the most common form of valvular heart diseases. MV regurgitation is characterized by reverse blood flow from the LV to the LA and high pressure gradients across the mitral valve during systole. In severe cases, a surgical intervention may be necessary to repair, or even replace the incompetent valve. Suturing the two mitral leaflets together at the regurgitant hole may help patients with severe mitral insufficiency due to leaflet prolapse or calcified annulus. In the percutaneous edge-to-edge technique, the leaflets are attached using a clip (e.g., MitraClip) delivered through a catheter.

Transthoracic echocardiography (TTE) is an imaging modality used for early detection and assessment of mitral regurgitation (MR). Ultrasound images, such as three-dimensional (3D) transthoracic images, may be used to evaluate MV function in patients. Color flow imaging on the TTE, for example, may reveal a jet of blood flowing from the LV into the LA during ventricular systole. With real-time full volume echocardiography, transthoracic B-Mode volumes are acquired along with 3D color flow imaging (CFI) for every heartbeat. A combination of measurements, based on both morphological and functional observations, is used to assess disease progression and make therapy decisions. However, the complexity of MV anatomy and its fast dynamics make accurate quantification of the MV anatomy from medical images difficult.

Automatic or semi-automatic methods have been proposed to make MV assessment more efficient. The shape and motion of the annulus or the mitral leaflets is modeled from transesophageal echocardiography (TEE) or computed tomography (CT) images. However, TEE is invasive and CT uses x-rays. These modeling approaches have not been designed to cope with images with considerable lower quality, such as TTE even though TTE imaging may be more simply performed.

BRIEF SUMMARY

By way of introduction, the preferred embodiments described below include methods, computer readable media and systems for detecting a mitral valve in transthoracic echocardiography (TTE). The ultrasound transducer is positioned against the chest of the patient rather than being inserted within the patient. While data acquired from such scanning may be noisier or have less resolution, the mitral valve may still be automatically detected. Using both B-mode data representing tissue as well as flow data representing the regurgitant jet, the mitral valve may be detected automatically with a classifier trained with machine-learning techniques. A series of classifiers may be used, such as determining a position, orientation and size (scale) of a valve region with one classifier, determining a regurgitant orifice with another classifier, and locating mitral valve anatomy with a third classifier. One or more features may be calculated based on the orientation of the valve region.

In a first aspect, a method is provided for detecting a mitral valve in transthoracic echocardiography. A transducer adjacent a patient scans a cardiac region of a patient with ultrasound. A B-mode detector detects, in response to the scanning, B-mode data representing tissue in the cardiac region. A flow estimator estimates, in response to the scanning, flow data representing fluid in the cardiac region. The flow data is energy, velocity, or energy and velocity. A processor (a) calculates feature values from both the B-mode data and the flow data, applies the feature values from both the B-mode data and the flow data to a first machine-learnt classifier, the first machine-learnt classifier indicating a global region of the mitral valve, the mitral valve comprising a tissue structure, (b) applies the feature values from both the B-mode data and the flow data to a second machine-learnt classifier, the second machine learnt classifier indicating a regurgitant orifice, the regurgitant orifice constrained to be within the global region of the mitral valve, (c) identifies a mitral annulus and closure line as a function of a third machine-learnt classifier and orientation and scale of the global region, and (d) transforms a statistical shape model as a function of the mitral annulus and closure line. A valve image is output to a display device where the valve image is a function of the transformed statistical shape model.

In a second aspect, a non-transitory computer readable storage medium has stored therein data representing instructions executable by a programmed processor for detecting a mitral valve in transthoracic echocardiography. The storage medium includes instructions for locating a position and orientation of a mitral valve region using tissue and flow ultrasound features input to a first classifier, calculating input features oriented based on the orientation of the mitral valve region, the input features calculated for locations in the mitral valve region, and determining a location of anatomy of the mitral valve in the mitral valve region in response to input of the oriented input features into a second classifier.

In a third aspect, a system is provided for detecting a mitral valve in transthoracic echocardiography. An ultrasound scanner is configured to scan a heart volume of a patient, the scan providing B-mode and Doppler flow data. A processor is configured to locate a regurgitant orifice structure of the mitral valve from the B-mode data and the Doppler flow data. The location is determined without user indication of a location of the mitral valve and without user indication of a location on an image. A display is configured to generate a visualization of the mitral valve with a highlight being a function of the regurgitant orifice structure.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
FIG. 1 shows example B-mode and flow mode images and an example fitted model image of the mitral valve.

Automatic detection and quantification of mitral regurgitation using TTE is provided. TTE may be used to acquire B-mode data and flow data. The left and center images of FIG. 1 show B-mode and Doppler velocity images. The mitral valve may be shown in the images, but is not very distinct or is difficult to locate. To assist the sonographer, the mitral valve or mitral valve anatomy may be detected and highlighted, such as shown in the right image of FIG. 1. In the center image, two versions are provided. In the right most version, a segmented 3D proximal iso-velocity surface area (3D PISA) is shown.

For automatic detection, a framework detects and quantifies mitral regurgitation with TTE data. 3D features are computed on multiple channels, including the volumetric anatomical (B-Mode) and hemodynamical (Color Doppler or flow) channels, to extract both morphological and functional information. Based on the extracted multi-channel features, a discriminative classifier is then trained through a boosting process to detect the MR jet position. In order to locate the associated mitral valve structure, such as the mitral valve annulus and the valve closure line, a statistical shape model is further integrated into the framework, and a constrained volume sub-sampling method is used to identify information to fit to the statistical shape model. Consequently, a patient-specific mitral valve model is obtained based on the detected mitral regurgitation and mitral valve locations. The anatomical structure is visualized to assist therapy planning and procedure simulation.

The mitral valve is a tissue structure. To detect this tissue structure, both tissue and flow information are used rather than just tissue information. The regurgitant jet is a flow structure. To detect the flow structure, both tissue and flow information are used rather than just flow information. In one embodiment, a learning-based method automatically locates and quantifies mitral regurgitation by leveraging information from both anatomical and hemodynamical data. Any number of stages may be provided, such as three stages: estimation of the global transformation of the mitral valve region, detection and segmentation of the mitral regurgitant jet, and localization of the mitral annulus and the valve closure line.

Figure 2:
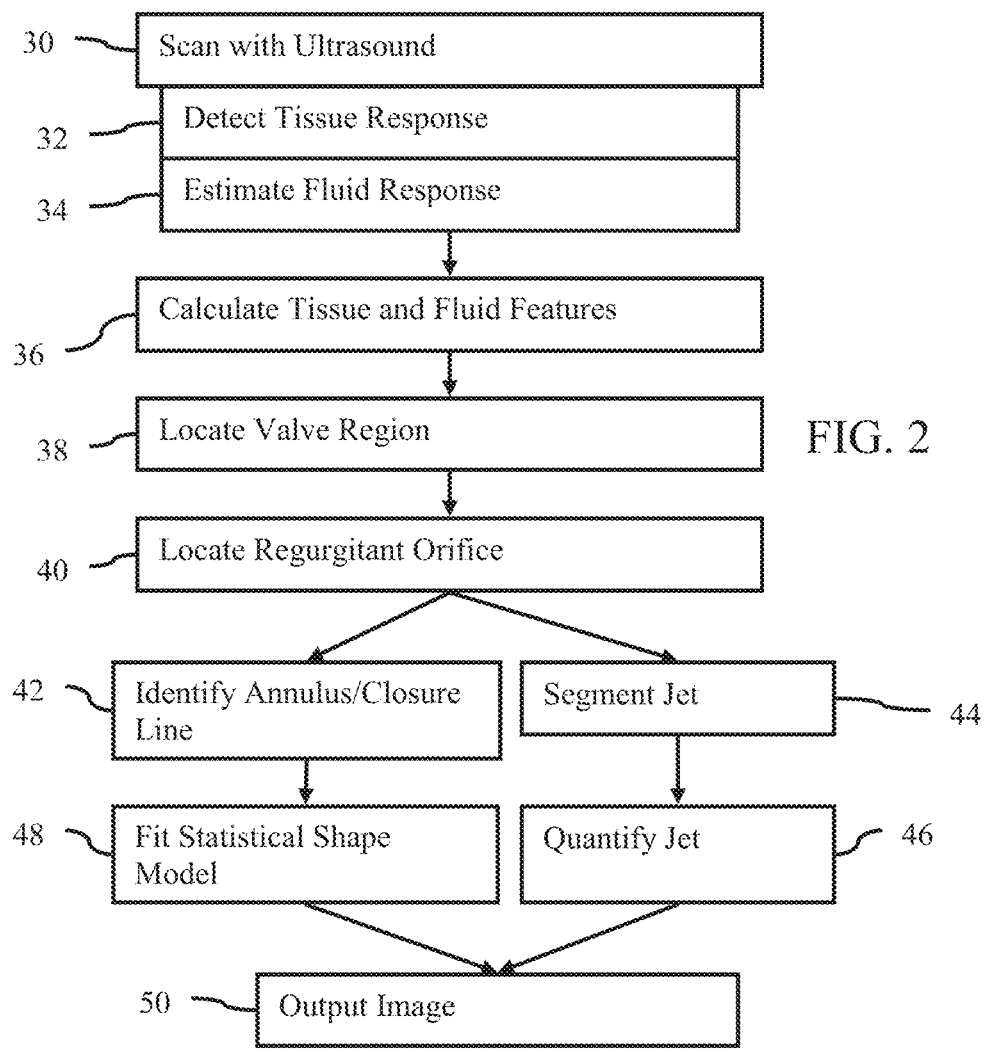
FIG. 2 is a flow chart diagram of embodiments of methods for detecting a mitral valve in transthoracic echocardiography.

FIG. 2 shows a method for detecting a mitral valve in transthoracic echocardiography. The method is implemented by a medical diagnostic imaging system, a review station, a workstation, a computer, a PACS station, a server, combinations thereof, or other device for image processing medical diagnostic data. For example, the system or computer readable media shown in FIG. 9 implements the method, but other systems may be used.

The method is implemented in the order shown or a different order. For example, act 42 may be performed prior to act 40. Additional, different, or fewer acts may be performed. For example, one or more of acts 30-36 and 50 are not provided. As another example, acts 44 and 46 are not performed. In other examples, any combination of two or more of acts 30, 36, 38 40, 42, and 48 are performed.

The acts are performed in real-time, such as during ultrasound scanning of act 30. The user may view images of act 50 while scanning in act 30 to acquire another dataset representing the cardiac volume. The acts may be performed during an appointment or off-line in a review period. The images may be associated with previous performance of one or more of the acts in the same imaging session. Measurements and/or images of automatically detected anatomy may be provided in seconds, such as 10 or fewer seconds. Alternatively, the acts are performed as desired by a surgeon regardless of whether a patient is currently at the facility or being scanned.

The acts are performed for diagnosis, planning, or other purpose. In one embodiment, the acts are performed prior to a mitral clipping or other repair procedure to assist in planning the procedure. The acts may be repeated or alternatively performed after the procedure to evaluate results of the procedure. Mitral regurgitation quantification provides pre and post MitraClip or other procedure measures. The average mitral regurgitation volume after a MitraClip procedure may be reduced compared to the pre-procedure value, confirming a good clinical outcome.

In act 30, a cardiac region of a patient is scanned with ultrasound. An ultrasound transducer, such as an array of 32, 64, 128, 256 or other number of elements, is positioned against the patient. For transthoracic echocardiography, the transducer is positioned on the chest of the patient such that the acoustic energy passes between ribs of the patient to scan the heart or portion of the heart. A handheld or machine positioned probe is used on the skin surface of the patient. The scanning is performed without inserting the transducer into the patient, such as without transesophageal or cardiac catheter imaging. In alternative embodiments, transesophageal or cardiac catheter ultrasound imaging is used.

Any format for scanning may be used, such as linear, sector, Vector®, or other format. The distribution of scan lines is in three-dimensions to scan a volume of the cardiac region. The volume is scanned using electronic and/or mechanical steering (e.g., wobbler array). The transducer is held in place or moved to scan the volume.

The scanning transmits acoustic energy. In response to the transmissions, acoustic echoes are received. Different structures or types of structures react to the acoustic energy differently. Using beamforming, the cardiac region is sampled. For rapid volume scanning, plane wave or broad transmit beams are formed. Multiple, such as 4, 8, 16, 32, 64, or other number, of receive beams are formed in response to each transmit beam. In alternative or additional embodiments, cardiac or ECG gating is used to scan in synchronization with the cardiac cycle. Transmissions and receptions from different cycles but at the same time relative to the cycle may be combined to sample the cardiac region.

For patient specific modeling, one or more sets of data are obtained by scanning. One or more sets represent the cardiac region at a same phase of the cardiac cycle (e.g., end-diastole or end-systole). Sets of data representing the volume multiple times during a heart cycle may be acquired by scanning. The ultrasound data corresponds to a data set interpolated to a regular 3D grid, displayed images (e.g., detected and scan converted ultrasound data), beamformed data, detected data, and/or scan converted data. The ultrasound data represents the volume or 3D cardiac region of the patient. The region includes tissue, fluid or other structures.

In act 32, the tissue response to the acoustic energy is detected. The receive beamformed samples are processed to represent the intensity of the echoes from the location. B-mode detection is performed. The B-mode data represents the tissue in the cardiac region. Using thresholding and/or filtering, signals associated with fluid are removed. Since the intensity of return from fluid is relatively small, B-mode data may include little or no signal from fluid. The distribution of B-mode data shows the shape of a structure or spatial aspect. The B-mode data is of the echoes at a fundamental (transmit) frequency or a harmonic thereof (e.g., second harmonic). In alternative embodiments, Doppler tissue imaging or other mode is used to detect the tissue response.

In act 34, fluid response to the acoustic energy is detected. Flow data representing the fluid in the cardiac region is estimated. Since fluid is typically moving, the change associated with the movement may be used to represent the flow. Doppler processing, whether relying on the Doppler phenomena or based on other ultrasound processing, estimates the flow data. A shift in frequency may be used to estimate the energy, velocity, variance, or combinations thereof of the fluid. For example, the Doppler velocity is estimated as a velocity value or the shift frequency. Other flow estimation may be used, such as determining motion between samples from different times using correlation.

In alternative embodiments, the B-mode or tissue response data and the flow mode or fluid response data are acquired from a memory. Previously acquired information is loaded or received for further processing to detect the mitral valve.

A processor, such as associated with a computer, server, or dedicated detector, performs acts 36-50. The acts 36-50 are performed without further user input. The user may activate the process, such as configuring an ultrasound system for mitral valve detection and activating the process. The user may shift the transducer until images show the cardiac region likely to include the mitral valve, but the user does not indicate a location of the mitral valve on the images. The processor automatically identifies the mitral valve, mitral valve anatomy, and/or jet information without user input other than activation and scanning position. The user does not indicate the location of the mitral valve within the cardiac region. In alternative embodiments, a semi-automatic process is used where the user confirms or guides the process by indicating one or more locations.

To detect the mitral valve, tissue and fluid features are calculated in act 36. The features are not specific cardiac or mitral valve anatomy or jet features, but are features for input to a classifier. Anatomy or jet features may be used on input features for the classifier. Other features, such as the B-mode data and flow data or values derived there from, may be used.

The feature values for input to the classifier are calculated from both the B-mode data and the flow data. A given feature value may be derived from just B-mode or just flow data. For classification, input features from both the B-mode data and the flow data are input. A set of B-mode features is input, and a set of flow data features are input. In alternative or additional embodiments, a given input feature is a function of both types of data. In other embodiments, only B-mode or only flow mode data is used. Additional features, such as features not from scanning or images, may be used as well.

Due to the nature of mitral regurgitation, characterized by the reverse blood flow from the left ventricle (LV) to the left atrium (LA) and high pressure gradients across the mitral valve during systole, a combination of measurements based on both morphological and functional observations are used to assess disease progression and make therapy decisions. Recent advances in the real-time 3D echocardiography allow acquisition of volumetric anatomical and hemodynamical data in a single heart beat. The anatomical context is stored in the form of a B-Mode image IB, while the corresponding color flow image IC encodes the volumetric blood flow measurements with the magnitude of the flow velocity and direction relative to the ultrasound probe.

In order to extract both morphological and functional information, 3D features are computed for these multiple channels: volumetric anatomical (B-Mode) $I_{FB}$ and hemodynamical (color flow) $I_{FC}$. Single channel feature responses at each sampling point are concatenated to form a new feature vector $I_F = \{I_{FB}, I_{FC}\}$.

Any type of input features may be calculated. For example, gradients of the data, the data itself, detected anatomical or jet features of the data, maximum, minimum, other statistical, or other information are calculated from the B-mode and flow data. In one embodiment, 3D Haar wavelets and steerable features are used. These features are relatively fast to compute and capture information well.

Flow data is on a different scale than B-mode data. For example, the B-mode data has a 0-255 scale of possible intensities. Flow data is signed to represent flow to and away from the transducer. The range of the scale may be different such as −100 to 100. The input features may be calculated using the native scales. Alternatively, the feature values or the data used to calculate the feature values are scaled to compensate for the scale differences. For example, the flow data is transformed to the B-mode scale to have a same range. Other dynamic range adjustment may be used. The B-mode data may be transformed to the flow data scale or both may be transformed to a common scale.

Acts 38, 40, and 42/48 represent three sequential stages for mitral valve detection in a hierarchal model. Act 38 corresponds to estimation of a location of the global valve relative to the heart volume. Act 40 corresponds to estimating a jet location and/or orifice relative to other portions of the valve. Acts 42 and 48 correspond to estimation of an anatomy, a surface, curve, or other shape of the valve. Each stage may use the same or different algorithms. For example, separate machine-learnt algorithms are used. Additional, different, or fewer stages may be used. For example, one or more stages are combined into a single classifier. Parallel rather than sequential processing may be used. The stages may be performed in other orders.

In act 38, the global mitral valve anatomy is localized. A position, orientation, and/or scale of the mitral valve region within the cardiac or scan region is located. The global mitral valve anatomy is the entire mitral valve or a portion of the mitral valve without being a specific part and/or with being a collection of multiple parts. The mitral valve as distinguished from heart wall, other valves, or other heart anatomy is located.

Figures 3A, 3B, 3C:
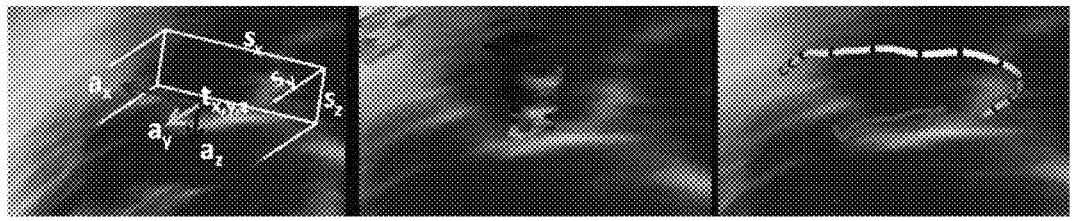
FIGS. 3A-C show example B-mode images for a global valve region (FIG. 3A), a regurgitant orifice (FIG. 3B), and estimated annulus and closure line fittings (FIG. 3C)

A bounding box, sphere, segmented surface, or other shape is used to designate the global mitral valve anatomy. In one embodiment, the global location of the mitral valve anatomy is represented by a bounding box parameterized with an affine transformation. The bounding box θ is parameterized for translation T (position), rotation R (a), and scale S along the three dimensions of the volume. θ=(T, R, S)=(tx, ty, tz, ax, ay, az, sx, sy, sz). FIG. 3A illustrates an example bounding box. Other parameterizations may be used, such as with just translation and rotation (not scale) or with one or more aspects limited to fewer than three dimensions.

In this representation, the position of the bounding box is given by the barycenter of the mitral valve. Other indications of position, such as a corner of the box, may be used. The scale is chosen to enclose the entire underlying mitral valve anatomy. The shape or scale may include other information, such as including tissue from adjacent structures of the heart and/or part or all of the regurgitant jet. The orientation is defined by the mitral trigonal plane. Other references for scale and/or orientation may be used.

The global mitral valve anatomy, such as represented by the bounding box, is located using some or all of the input features calculated in act 36. The tissue ultrasound features derived from B-mode data and the flow ultrasound features derived from Doppler data (e.g., derived from velocity) are used to locate the mitral valve. Some features may be more determinative of location, rotation, and/or scale than others. Some features may not be used for global localization. Since the view angle and other scan parameters may vary from scan to scan, all of the calculated input features may be used.

The global position of the mitral valve is located by a classifier. The feature values are input to the classifier, and the classifier outputs the bounding box, parameter values, or other indicator of the global position of the mitral valve. The classifier is a machine learnt classifier. Based on the extracted 3D multi-channel features, a discriminative classifier or classifiers are trained to detect the location of the mitral valve.

Other discriminative classifiers may be used for other detections, such as for locating the regurgitant orifice, mitral annulus, and/or mitral valve closure line. To achieve robust and accurate detection results, the search is performed in a hierarchical manner. The global location of the mitral valve anatomy of act 38 uses one classifier, followed by the estimation of associated mitral jet, such as the mitral regurgitant orifice in act 40 using another classifier, and the mitral annulus and the mitral valve closure line in act 48 using another classifier. The same or different types of classifiers may be used. Since the classifiers are used for different purposes, the resulting machine-learnt classifier for one stage is different than for another stage even if using a same type.

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, tens or hundreds of volume sequences representing the heart and including the mitral valve are annotated. The annotation indicates valve landmarks, jets, global locations, surfaces, or other relevant information within the volumes. The anatomies of each volume are annotated. This large number of annotations allows use of a probabilistic boosting tree to learn relevant features over a large pool of 3-D Haar and/or steerable features. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the anatomies and/or measurement indicators for the anatomies. The detectors are trained on a large number of annotated 3D volumes. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different resolutions, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features.

A tree structure may be learned and may offer efficiency in both training and application. Often, in the midst of boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques, such as disclosed by U.S. Pat. Nos. 7,702,596 and 7,916,919.

In one embodiment of the classifier for global mitral valve localization, a marginal space learnt classifier is applied. The global region is located in stages or with sequentially determined translation, rotation, and scale along three-dimensions. The position within the volume is first classified, and then the rotation at that position is classified, followed by the scale given the position and rotation. The machine-learned matrix finds position candidates around the mitral valve based on Haar-and steerable features. The position candidates are then successively refined by rotation and scaling candidates. This defines a region of interest for the mitral valve, such as the bounding box.

In one embodiment, this global localization task is formulated as a classification problem for which a discriminative detector DO is trained using the probabilistic-boosting tree (PBT) approach. The affine parameters of θ are determined efficiently by searching the subsets with an increasing dimensionality using the Marginal Space Learning (MSL) method. The discriminative detector is represented as $p(\theta|I_F)=p(T|I_F) p(R|T, I_F) p(S|R, T, I_F)$ where p is a probability from the PBT. FIG. 3A shows an example of a bounding box with translation, rotation, and scale determined by a MSL-based PBT machine-learnt classifier.

In act 40, the regurgitant orifice or regurgitant orifice is located. When the mitral valve is closed, most or all backflow of blood is prevented. Where the mitral valve is not operating properly, one or more orifices in the closure line where the valve leaflets meet occur. The regurgitant flows through the orifice or orifices, causing the regurgitant jet or jets.

In order to detect and quantify the mitral regurgitation, it is important to find the location of the mitral valve regurgitant orifice, $L(I_x, I_y, I_x)$, where the abnormal leaking of blood occurs. Locating the regurgitant orifice may be a challenging task due to the limited resolution and low signal-to-noise ratio at the mitral valve region in the transthoracic echocardiography data.

A machine-learnt classifier is used to locate the regurgitant orifice. Any of the machine-learnt classifiers discussed above may be used. Any input features may be used, such as applying both feature values from B-mode data and feature values from flow data. In response to inputting the feature values, the matrix embodying the classifier outputs a location of the regurgitant orifice.

The regurgitant orifice is located independently of the global localization or is located based, at least in part, on the global localization. For example, the bounding box indicating the mitral valve is used as a constraint. The regurgitant orifice is constrained to be in the bounding box, not outside the bounding box. As another example, the parameters from the global localization (e.g., T, R, and/or S) are used as input features.

In one embodiment, a position detector is trained with PBT and 3D multi-channel features computed in act 36 (both features from tissue response and features from fluid response) to form a strong classifier DL. The trained classifier DL returns a peak posterior probability $p(I_x, I_y, I_z | I_F)$ at the regurgitant location and a low probability score if there is not regurgitant jet in the image or at the location. To remove outliers, the position L of the mitral regurgitant orifice is constrained to be within the global location of the mitral valve anatomy. The constraint optimizes the joint probability, $\arg\max_L p(L|I_F) p(L|\theta)$. The joint probability is a function of the different machine-learnt classifiers. The joint probability may not be calculated, but the constraint acts to weight the localization of the regurgitant orifice. The resulting probability from the regurgitant orifice classifier is a joint probability (e.g., function of both classifiers).

FIG. 3B shows a detected regurgitant orifice as a dot. The dot is at the base of a mitral regurgitant jet. More than one regurgitant orifice may be located. Thresholding or other processes may be used to select the regurgitant orifice with the greatest probability or to select the desired number of regurgitant orifices. Other processes may be used to determine the desired regurgitant orifice from a list of possibilities. The regurgitant orifice is located automatically using the classifiers. The regurgitant orifice is located free of user indication of a location in a cardiac image.

In act 44, the regurgitant orifice is used to segment the mitral regurgitation jet. The detected mitral regurgitant orifice L is used as a seed point to segment the jet. Any process for segmentation may be used. The regurgitant orifice may be associated with a velocity. Any velocities within a range are treated as part of the jet. The resulting spatial distribution may be filtered. In another embodiment, an iso-velocity region is segmented based on the color Doppler data. Because a main characterization of the mitral regurgitation is the reverse blood flow from the LV to the LA, a random walker algorithm may be used to segment the jet. The direction from LV to LA is used to indicate on which side of the mitral valve to search for the jet. By incorporating the direction constraint along the mitral regurgitant flow, the random walker locates a volume having the same or similar velocity. Other segmentation may be used.

In act 46, the mitral regurgitation jet from the segmentation is quantified. The velocity, a volume, a variance, a distribution, or other quantity is calculated. In one embodiment, an iso-velocity surface with a proximal iso-velocity surface area (PISA) is extracted. A surface associated with a same or similar velocity in the jet is found. For example, the marching cubes algorithm is applied to locate the PISA. The PISA is used to compute the mitral regurgitant volume and the effective regurgitant orifice area (EROA). For example, EROA= (PISA×flow velocity of PISA)/peak velocity of the jet over a cardiac cycle. As another example, the volume is an integration of the PISA×the flow velocity over time. Other quantities may be calculated.

In act 42, anatomy of the mitral valve is identified. For example, the mitral annulus and/or closure line are identified. In other examples, other anatomies, such as leaflets and/or chordae, are identified. Any part of the mitral valve may be located. Given the identified mitral valve region, anatomical structures of interest, such as the mitral annulus and the closure line, are detected.

Any representation may be used for identification. For example, the mitral annulus and closure line are represented as fit curves or detected surfaces. In one embodiment, the location and shape of the mitral annulus and closure line are parameterized by a point distribution model, $M_{ac} = \{M_a = (a1, \ldots, an), M_c = (c1, \ldots, cn)\}$, where c is the closure line and a is the annulus. Any number of points n may be used, such as n=30.

Another machine-learnt classifier is used to identify the anatomic structure or structures. Any of the classifiers discussed above, but trained for locating specific anatomic structure of the mitral valve may be used. The classifier locates the entire structure. Alternatively, different points are sequentially classified. The global mitral valve region is searched point by point. For each point, input features for the point and surrounding points are used to classify the probability that the point is part of the annulus and/or closure line. The same or different classifiers are used for detecting the annulus and closure.

Any of the input features discussed herein may be used. In one embodiment, the input features from fluid response are not used. The input features from B-mode data are used without flow data features. The position of the mitral valve is used to constrain or guide identification of specific anatomic structure. The features for locations within the global region or bounding box are used and features for other locations are not used. Alternatively, features within a window function of the point being classified regardless of position within or not of the bounding box are used.

The features are directional. For example, Haar or steerable features are directional. The orientation of the mitral valve, as reflected in the mitral valve region, is used for calculating or selecting the features. The orientation indicates more likely positioning or relationships of different anatomy. Scale may likewise be used to select or calculate the features. The bounding box parameters are used in feature calculation.

One challenge in detecting the mitral valve structure is the high appearance variation, due to the limited resolution and low signal-to-noise ratio at the mitral valve region as well as the rapid motion of the valve leaflets. Sample alignment may reduce intra-class variation with impact on classification results and speed object recognition. Instead of directly estimating the annulus and closure line parameters from the input image, a volumetric sampling scheme parameterized by the estimated global affine parameters θ is used.

Given the estimated global affine parameters θ, for each point in the shape model $M_{ac}$, a sub-volume $V_i$ is sampled in the space centered at the point location. The orientation and scale are defined with respect to the global transformation or bounding box. For each sub-volume $V_i$, pre-aligned 3D Haar-like features are computed. The size of the windowing function or sub-volume is controlled by the scale. The direction of the 3D Haar features is controlled by the orientation.

Figure 4:
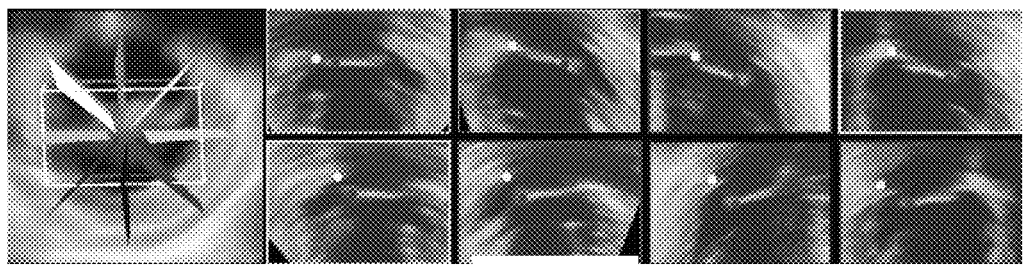
FIG. 4 shows example oriented sampling planes for classifying points as annulus or closure line locations.

FIG. 4 shows an example sampling of features based on orientation. The image on the left shows nine planes defined relative to the orientation of the bounding box. Any number of planes with equal or non-equal spacing may be used. Other plane orientations relative to the valve orientation may be used. Starting from a plane at the anterior commissure, a sequence of any number (e.g., 30) constrained sub-volumes $V_i$ for the anterior (FIG. 4—upper row) and the posterior (FIG. 4—bottom row) annulus and closure line are used to calculate the input features. The directional features are aligned with the direction of the sampling plane. From each volume $V_i$, pre-aligned 3D Haar-like features are computed.

The features are applied to a matrix representing a machine-learnt classifier. In one embodiment, the classifier is a PBT classifier, so provides the target posterior probability: $p(M_i|t_x,t_y,t_z,V_i)=Di(t_x,t_y,t_z, V_i)$, $(t_x,t_y,t_z)$ in the set of $V_i$ where $p(M_i|t_x,t_y,t_z, V_i)$ is the probability of having a 3D annulus or closure line point at the location $(t_x,t_y,t_z)$ within $V_i$.

Consequently, the valve region θ and the anatomy shape $M_{ac}$ are optimized together on an input image I by maximizing the following joint probability, arg max $p(θ, M_{ac}|I)$=arg max$_{θ, Mac}$ $p(θ|I)p(M_{ac}|$74 , I)=arg max$_{θ, Mac(i)}$ $P(θ|I)π_i P(M_{ac}^{(i)}|θ, I)$ where $M_{ac}^{(i)}$ is the i-th point of the anatomy shape i model $M_{ac}$.

The points with the highest probability, probability over a threshold, or other criteria are selected as representing the mitral annulus and/or closure line. Points with lesser probabilities are not selected. The classifier outputs the probabilities for each point tested, and the points with the greater or sufficient probability are used as indicating the anatomy. The mitral annulus and closure line are represented as discrete ones of the points with relatively greater probabilities.

The detected anatomy may be used as the output. The variance may be great due to the resolution of the data. For example, FIG. 3C shows a B-mode image with the closure line and annulus highlighted. There is little direct correlation of the highlighted or detected lines to the B-mode structure shown. Since the valve moves rapidly and is relatively small as compared to the resolution of ultrasound, a patient-specific valve model is fit to the detected closure line and annulus. A patient-specific valve model is fit to the input image to visualize the valve anatomy and to assist therapy planning and procedure simulation.

In act 48, a mitral valve model is fit to the patient specific information, providing the patient specific valve model. Any model of the mitral valve may be used, such as a theoretical or programmed model. In one embodiment, a statistical shape model is used. A statistical shape model of the mitral valve is built from a training set. Any number of samples may be used to determine the position and/or deviation probabilities for the mitral valve anatomy. A mesh, feature collection, sample grid or other distribution is used to represent the model.

The model is labeled. The anatomy is indicated by the model, such as indicating a position of the posterior leaflet, the anterior leaflet, the annulus, and the closure line. The model provides detailed information missing from, not easily viewable, or also included in the data representing the patient. For example, the closure line and annulus are not easily viewable in B-mode images. The model clearly indicates the locations for the closure line and annulus. In alternative embodiments, no labeling is provided.

The model is transformed to a patient-specific model. The model is altered or fit to patient-specific data. For example, a statistical shape model is transformed using the mitral annulus and closure line. Mitral annulus and closure line points from the statistical shape model are transformed to fit with annulus and closure line points from the classification of act 42. The spatial distribution probabilities of the statistical model may limit the transform so that the annulus and closure line more likely represent the norm or possible arrangements. Given the previously estimated mitral annulus and closure line, a patient-specific mitral valve model is constructed to visualize the anatomical structure.

Any fitting may be used. For example, thin-plate-spline, Gaussian bending, non-linear ICP, or other non-rigid transforms are applied. In one embodiment, a number (e.g., 13) of points identified as being on the 3D annulus and closure line are selected from both the statistical shape model and the patient anatomy shape model $M_{ac}$. Rather than using points identified as part of the detection of act 42, the annulus and closure line may be resampled for the transformation. The selected points are equally spaced along the annulus and closure line. These anchor points are used to compute the Thin-Plate-Spline (TPS) transformation, which deforms the valve model (e.g., statistical shape model) non-linearly to fit the anatomy shape model $M_{ac}$. Just the annulus and closure line are transformed. In other embodiments, other parts of the model are transformed based on the transformation of the annulus and closure line. In other embodiments, other structures instead of or in addition to the annulus and closure line are used for transformation.

The fit statistical shape or other model provides the location of the labeled anatomy, surface, or other mitral valve information specific to the patient. FIG. 3C shows estimated a mitral annulus and a closure line with fitted curves from the statistical shape model. The TTE image has highlighting added to show the closure line and annulus, which are otherwise not as clearly indicated.

In act 50, a valve image is output to a display device. The image is from the acquired scan data and/or from the fit model. For example, a combination image is generated where B-mode data shows tissue, flow data indicates fluid, and a mesh, labels, points, coloration, brightness or lines from the fit model highlight the valve. Alternatively or additionally, the image displays a value or other quantification. The image may be dynamic, showing the motion of the valve.

The image is a rendering of a three-dimensional volume. Voxels or data representing three-dimensional locations are rendered to a two-dimensional view. Ray casting, projection, surface or other rendering may be used. The viewing direction is from the left atrium looking at the valve. Other viewing directions may be used and chosen interactively by the user.

The image includes highlighting. The highlighting is in addition to the gray scale mapped B-mode and the color mapped flow mode data. The highlighting is a different color, brightness, resolution, graphic, or other characteristic to show a feature more prominently than otherwise occurs with TTE imaging. The highlighting may be a graphic overlay or is an alteration of the data mapped to display values. The highlighting may be of a surface, of a particular anatomy, of a curve, a label, a point, or of other details of the mitral valve. The fitted model indicates the location and/or what to highlight.

The mesh determined by the modeling may be used to surface render the valve. The mesh is an outline or surface, but other outlines, such as interconnected landmarks, may be displayed. In alternative embodiments, the image is of the landmarks or a representation of a valve fit to the mesh or landmarks.

In one embodiment, the model information is overlaid on a rendering of the heart or valves. The valve images are rendered from medical data with a same scale and perspective as an outline overlaid on the rendering. Color coding or other display modulation may be used with or in addition to an overlay. For example, different surfaces of the valve are rendered from B-mode data in gray scale with color modulation specific to the fitted model surface. One surface may be rendered in one color and another in another color. One rendering or multiple renderings from the same volume may be displayed. In one embodiment, a sequence of images is displayed. The sequence is rendered from the different volumes throughout a portion (e.g., simulating closure) or entire heart cycle.

Figure 5:
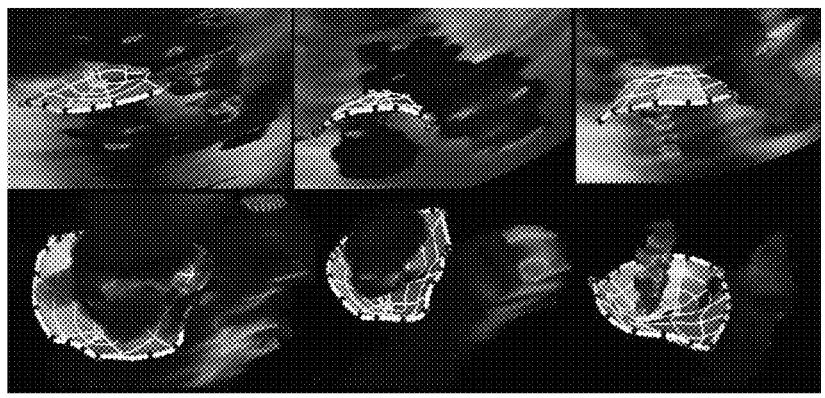
FIG. 5 shows example images of the mitral valve with fitted models.

FIG. 5 shows six example combination images of the fitted mitral valve model overlaid with a combination B-mode/flow mode image. The mitral valve model is estimated in the systolic phases of the cardiac cycle since the mitral valve is closed in systolic phases. The top row shows the estimated mitral valve model superimposed onto the TTE data. In the bottom row, the mitral valve model reveals the anatomical context information to highlight the mitral regurgitation jet in the volume color flow images. The rows are views from different directions. The left most pair of images shows more severe regurgitant jetting, the center moderate, and the right mild.

The regurgitant jet is shown by the color flow information. In other embodiments, the segmentation is used to further highlight the jet. Rather than using color mapping of velocity alone, locations associated with a mesh, iso-velocity, or detected surface may be highlighted to show the jet with more emphasis relative to other flow.

Figure 6:
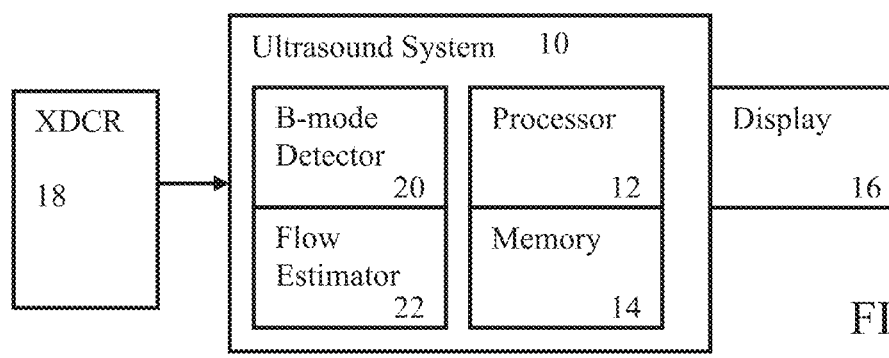
FIG. 6 is a block diagram of one embodiment of a system for detecting a mitral valve in transthoracic echocardiography.

FIG. 6 shows a system for detecting a mitral valve in transthoracic echocardiography. The system includes a transducer 18, an ultrasound scanner 10, and a display 16. The ultrasound scanner 10 includes a B-mode detector 20, a flow estimator 22, a processor 12, and a memory 14. In other embodiments, the system is a workstation, computer, or server for detecting using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for detecting. Additional, different, or fewer components may be used.

The ultrasound scanner 10 includes a transmit beamformer, receive beamformer, B-mode detector 20, flow estimator 22 (e.g., Doppler detector), harmonic response detector, contrast agent detector, scan converter, filter, combinations thereof, or other now known or later developed medical diagnostic ultrasound system components. As another example, the transducer 18 is not provided, such as where the system is a workstation for off-line or later measurement of valve anatomy.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension. In another embodiment, the array is a one-dimensional array. Multi-dimensional arrays or a plurality of one-dimensional arrays may be provided.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rocking an array or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart or valve volume. The scan may be repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., Doppler mode), contrast agent, harmonic, or other ultrasound modes of imaging. For valve detection, both B-mode and flow or Doppler mode data are acquired.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart or valve volume. The heart volume includes at least the mitral valve, but other portions of the heart may be represented. The memory 14 stores flow (e.g., velocity, energy or both) and/or B-mode ultrasound data. Alternatively, the medical image data is transferred to the processor 12 from another device. The medical image ultrasound data is a three-dimensional data set, or a sequence of such sets. The data represents a three-dimensional region.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging. For example, real-time imaging is provided by generating the images substantially simultaneously with the acquisition of the data by scanning. While scanning to acquire a next or subsequent set of data, images and fit model are generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring and/or generating a planar reconstruction without concurrent acquisition.

The memory 14 is additionally or alternatively a non-transitory computer readable storage medium with processing instructions. The memory 14 stores data representing instructions executable by the programmed processor 12 for detecting a mitral valve in transthoracic echocardiography. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein, such as controlling scanning, calculating features, detecting anatomy, measuring anatomy, and/or controlling imaging.

The processor 12 may perform machine learning and/or applies a machine-learnt algorithm. For example, the processor 12 applies a probabilistic model to detect valve anatomy. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different anatomy. The probabilistic models may be joint or dependent. The location of other anatomies or jets is used to limit or define a search space for a current anatomy and/or as a feature input for classification of another anatomy.

The different classifiers are the same or different types of classifiers. The same or different types of classifiers may be used for the same type of classification, such as different types of classifiers being used for different marginal space classification (e.g., the classifier for global translation is different than the classifier for global rotation).

In one embodiment, the probabilistic model is formed from a plurality of probabilistic boosting tree classifiers. Separate training and resulting machine-trained classifiers are provided for different aspects to be detected. For example, separate probabilistic boosting tree classifiers are provided for each of the marginal space types.

For application, the processor 12 calculates features for classification. The same or different features are used for classification in each stage. The features are three-dimensional features. 3D data defined by a window function is used to calculate the features. The window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. Other types of features may alternatively or additionally be used.

In one embodiment, the processor 12 is configured to implement one or more of the acts of FIG. 2. In other embodiments, the processor 12 is configured to locate the mitral valve, jet, or mitral valve and jet within a volume. The position, orientation, and/or scale of the mitral valve are determined. The processor 12 is configured to locate a regurgitant orifice from the B-mode data and the Doppler flow data. The location is determined based on or constrained by the mitral valve location. The locations are determined without user indication of a location of the mitral valve and without user indication of a location on an image. Automatic detection of the orifice is provided. Alternatively or additionally, the processor 12 is configured to locate a closure line and/or annulus. The closure line and annulus are located with input features calculated based on the orientation of the mitral valve. Directional features are aligned based on the valve orientation, such as being directed relative to the mitral trigon plane. The calculated features are input into a machine-learnt classifier.

The processor 12 is configured to use the located valve, orifice, annulus, and/or closure line. For example, the location of the valve is used to limit or constrain detection of the orifice, annulus, and/or closure line. As another example, the orientation and/or scale of the valve are used to select features to be input for classification. In other examples, the located annulus and/or closure are used to fit a model to the patient. In yet another example, a display is generated with the anatomy indicated relative to an ultrasound image. A quantity may be calculated and output on the image display.

The processor 12 is configured to generate an image. The fit model, identified anatomy, or other information (e.g., mesh locations or quantities) is used to generate the image. The patient-specific scan data may be used for imaging. The image provides a visualization of the mitral valve. The visualization may be of the valve prior to treatment or may be of the valve after treatment. The image may include the regurgitant jet.

The display 16 is a CRT, LCD, plasma, projector, printer, or other output device for showing an image. The display 16 displays an image of the detected anatomy, such as an image of a valve rendered from medical data and overlaid or highlighted based on the estimates of the valve position or other valve anatomy. The display 16 generates a visualization of the mitral valve with highlighting. The highlighting is color, brightness, or other modification to show the regurgitant jet, mitral valve, mitral valve anatomy, or regurgitant orifice structure.

The visualization may be generated during a same examination session as the scan. The detected anatomy may or may not be segmented, such as just displaying the valve and/or jet. Alternatively or additionally, the displayed valve may be based on the statistical model, so be different than the anatomy or scan data alone. A value of a measurement may be displayed. The value may be displayed in a chart, graph, and/or on an image.

To demonstrate performance, the method of FIG. 2 is performed using TTE datasets acquired from clinical studies of mitral regurgitation patients undergoing the MitraClip procedure. Volume TTE data is acquired by a Siemens SC2000 scanner with an average volume rate of 17 fps. The volume size varies from 124×131×120 to 235×235×166 with an average resolution of 1.6 mm per voxel. To evaluate the robustness and accuracy, the dataset is split randomly into a training and a testing set, with 36 and 10 cases respectively. The error is computed as the Euclidean distance between the MR orifice location detected in act 40 and the expert annotation on the same volume. The training and testing errors show a high accuracy performance, given that the average data resolution is about 1.6 mm per voxel. Comparing the MR jet volume VMR and the effective regurgitant orifice area (EROA) against the expert measurements, a correlation score of 0.8 results for both measures.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for detecting a mitral valve in transthoracic echocardiography, the method comprising the acts of:
    scanning, with a transducer adjacent a patient, a cardiac region of a patient with ultrasound;
    detecting, with a B-mode detector and in response to the scanning, B-mode data representing tissue in the cardiac region;
    estimating, with a flow estimator and in response to the scanning, flow data representing fluid in the cardiac region, the flow data comprising energy, velocity, or energy and velocity;
    calculating, with a processor, feature values from both the B-mode data and the flow data;
    applying, with the processor, the feature values from both the B-mode data and the flow data to a first machine-learnt classifier, the first machine-learnt classifier indicating a global region of the mitral valve, the mitral valve comprising a tissue structure;
    applying, with the processor, the feature values from both the B-mode data and the flow data to a second machine-learnt classifier, the second machine learnt classifier indicating a regurgitant orifice, the regurgitant orifice constrained to be within the global region of the mitral valve;
    identifying, with the processor, a mitral annulus and closure line as a function of a third machine-learnt classifier and orientation and scale of the global region;
    transforming, with the processor, a statistical shape model as a function of the mitral annulus and closure line; and
    outputting to a display device a valve image, the valve image being a function of the transformed statistical shape model.

2. The method of claim 1 wherein scanning comprises performing transthoracic echocardiography, wherein detecting comprises detecting intensities of acoustic echoes from tissue, and wherein estimating comprises estimating Doppler velocity.

3. The method of claim 1 wherein calculating the feature values comprises calculating Haar, steerable, or Haar and steerable feature values for the B-mode data and for the flow-data.

4. The method of claim 1 wherein applying to the first machine-learnt classifier comprises applying to a marginal space learnt classifier, the global region indicated with sequentially determined translation, rotation, and scale along three-dimensions.

5. The method of claim 1 wherein applying to the second machine-learnt classifier comprises automatically locating the regurgitant orifice free of user indication of location in a cardiac image.

6. The method of claim 1 wherein the regurgitant orifice has a joint probability that is a function of the first and second machine-learnt classifiers.

7. The method of claim 1 further comprising:
    segmenting a mitral regurgitation jet with the regurgitant orifice as a seed; and
    quantifying the mitral regurgitation jet from the segmenting.

8. The method of claim 1 wherein identifying the mitral annulus and closure line comprises sequentially classifying points in the global region with input features of the third machine-learnt classifier being determined as a function of the orientation and the scale, the mitral annulus and closure line comprising discrete ones of the points with relatively greater probabilities.

9. The method of claim 1 wherein transforming comprises fitting modeled annulus and modeled line from the statistical shape model to the mitral annulus and closure line with a thin plate spline.

10. The method of claim 1 wherein outputting comprises outputting the valve image as a three-dimensional rendering with at least one anatomical location of the mitral valve highlighted relative to other tissue, the at least one anatomical location determined from the transformed statistical shape model.

11. The method of claim 1 wherein outputting comprises outputting the valve image with a regurgitant jet in the valve image.

12. The method of claim 1 wherein the acts are performed prior to a mitral clipping procedure and are repeated after the mitral clipping procedure.

* * * * *